United States Patent [19]
Becker et al.

[11] Patent Number: 5,772,659
[45] Date of Patent: Jun. 30, 1998

[54] ELECTROSURGICAL GENERATOR POWER CONTROL CIRCUIT AND METHOD

[75] Inventors: Daniel J. Becker, Broomfield, Colo.; Michael Steve Klicek, Troy, Mich.

[73] Assignee: Valleylab Inc., Boulder, Colo.

[21] Appl. No.: 533,891

[22] Filed: Sep. 26, 1995

[51] Int. Cl.$^6$ ...................................................... A61B 17/38
[52] U.S. Cl. .................................................. 606/34; 322/7
[58] Field of Search ................................. 606/34, 35, 38, 606/32, 42; 322/7, 27, 44; 323/322, 340, 911, 312, 315

[56] References Cited

U.S. PATENT DOCUMENTS

| | | |
|---|---|---|
| 3,601,126 | 8/1971 | Estes . |
| 3,913,583 | 10/1975 | Bross ......................................... 606/35 |
| 3,964,487 | 6/1976 | Judson . |
| 3,980,085 | 9/1976 | Ikuno . |
| 4,092,986 | 6/1978 | Schneiderman . |
| 4,126,137 | 11/1978 | Archibald . |
| 4,188,927 | 2/1980 | Harris . |
| 4,658,819 | 4/1987 | Harris et al. . |
| 4,727,874 | 3/1988 | Bowers et al. . |
| 4,961,047 | 10/1990 | Carder ................................... 606/35 X |

Primary Examiner—Jennifer Bahr
Assistant Examiner—Ryan Carter
Attorney, Agent, or Firm—Peter C. Richardson; Lawrence C. Akers; Aaron Passman

[57] ABSTRACT

A constant power control circuit for an electrosurgical generator and a method for maintaining the electrical power output of an electrosurgical generator at a generally constant value throughout a given tissue impedance range are disclosed. The constant power control circuit and the method recognize and use the unique and simple linear characteristics associated with certain electrosurgical generator designs to monitor and control the electrical power output without having to calculate or monitor the actual output power. The constant power control circuit includes a current sampling circuit, a linear conversion circuit, and a feedback correction circuit. The constant power control circuit may also include protection circuitry that prevents the electrosurgical generator from being over-driven during high and/or low impedance loading, and reduces the severity of exit sparking by providing a quick response to high impedance indications while nonetheless maintaining increased power levels throughout a preset, nominal impedance range. The constant power control circuit and method may be included as an integral part of the overall electrosurgical generator's circuitry, or may be embodied as a separate unit that connects to, and controls, an electrosurgical generator. The constant power control circuit and method may be embodied through a variety of analog and/or digital circuit components or arrangements, including software running on computational and memory circuitry.

9 Claims, 3 Drawing Sheets

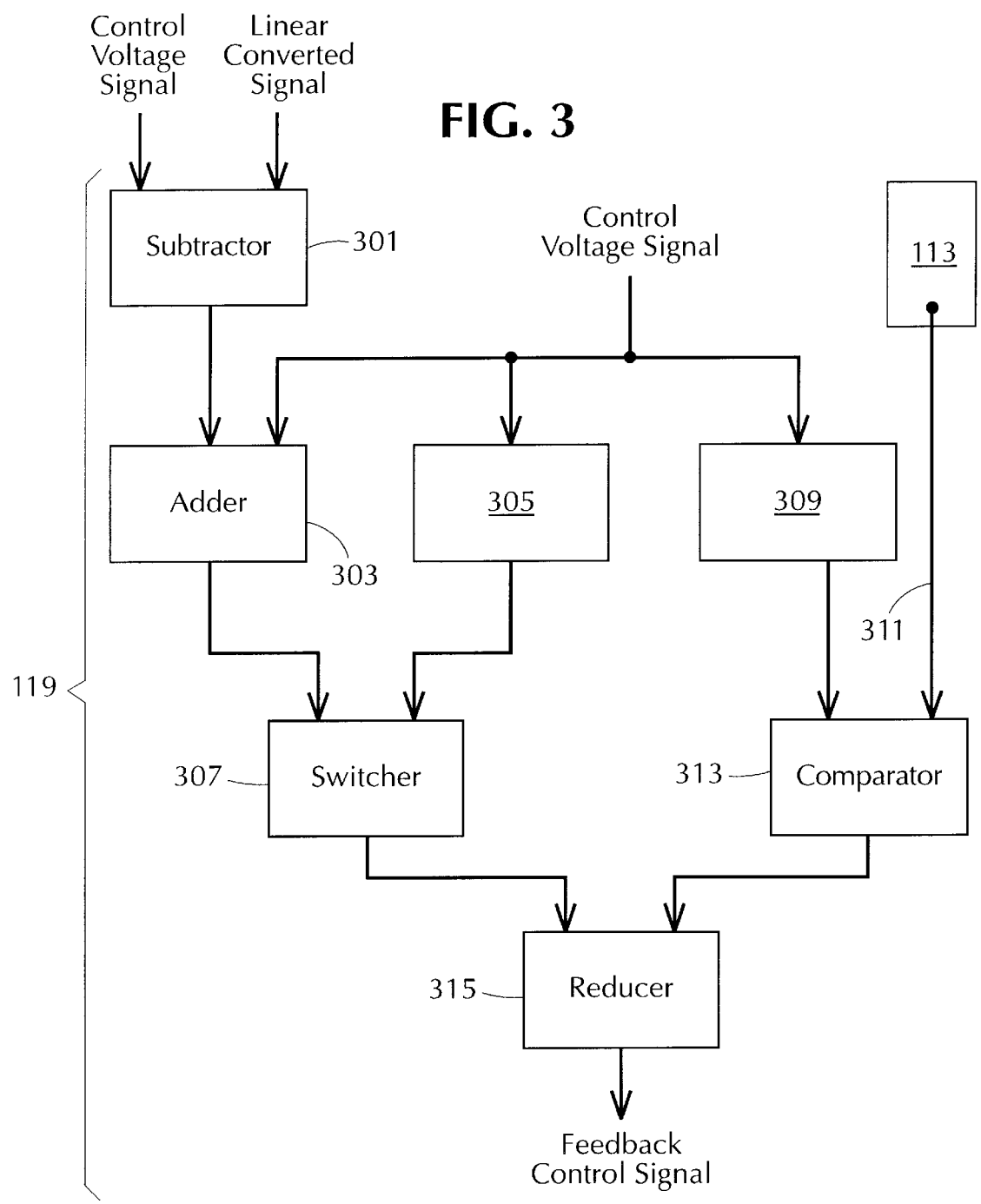

ELECTROSURGICAL GENERATOR POWER CONTROL CIRCUIT AND METHOD

FIELD OF THE INVENTION

A constant power control circuit for an electrosurgical generator and a method for maintaining the electrical power output of an electrosurgical generator at a generally constant level throughout a given tissue impedance range.

BACKGROUND OF THE DISCLOSURE

An electrosurgical generator is used in surgical procedures to deliver electrical energy to the tissue of a patient. An electrosurgical generator often includes a radio frequency generator and its controls. When an electrode is connected to the generator, the electrode can be used for cutting or coagulating the tissue of a patient with high frequency electrical energy. During normal operation, alternating electrical current from the generator flows between an active electrode and a return electrode by passing through the tissue and bodily fluids of a patient.

The electrical energy usually has its waveform shaped to enhance its ability to cut or coagulate tissue. Different waveforms correspond to different modes of operation of the generator, and each mode gives the surgeon various operating advantages. Modes may include cut, coagulate, a blend thereof, desiccate, or spray. A surgeon can easily select and change the different modes of operation as the surgical procedure progresses.

In each mode of operation, it is important to regulate the electrosurgical power delivered to the patient to achieve the desired surgical effect. Applying more electrosurgical power than necessary results in tissue destruction and prolongs healing. Applying less than the desired amount of electrosurgical power inhibits the surgical procedure. Thus, it is desirable to control the output energy from the electrosurgical generator for the type of tissue being treated.

Different types of tissues will be encountered as the surgical procedure progresses and each unique tissue requires more or less power as a function of frequently changing tissue impedance. Even the same tissue will present a different load impedance as the tissue is desiccated.

Two conventional types of power regulation are used in commercial electrosurgical generators. The most common type controls the DC power supply of the generator by limiting the amount of power provided from the AC mains to which the generator is connected. A feedback control loop regulates output voltage by comparing a desired voltage with the output voltage supplied by the power supply. Another type of power regulation in commercial electrosurgical generators controls the gain of the high-frequency or radio frequency amplifier. A feedback control loop compares the output power supplied from the RF amplifier for adjustment to a desired power level. Generators that have feedback control are typically designed to hold a constant output voltage, and not to hold a constant output power.

U.S. Pat. Nos. 3,964,487; 3,980,085; 4,188,927 and 4,092,986 have circuitry to reduce the output current in accordance with increasing load impedance. In those patents, constant voltage output is maintained and the current is decreased with increasing load impedance.

U.S. Pat. No. 4,126,137 controls the power amplifier of the electrosurgical unit in accord with a non linear compensation circuit applied to a feedback signal derived from a comparison of the power level reference signal and the mathematical product of two signals including sensed current and voltage in the unit.

U.S. Pat. No. 4,658,819 has an electrosurgical generator which has a microprocessor controller based means for decreasing the output power as a function of changes in tissue impedance.

U.S. Pat. No. 4,727,874 includes an electrosurgical generator with a high frequency pulse width modulated feedback power control wherein each cycle of the generator is regulated in power content by modulating the width of the driving energy pulses.

U.S. Pat. No. 3,601,126 has an electrosurgical generator having a feedback circuit that attempts to maintain the output current at a constant amplitude over a wide range of tissue impedances.

None of the aforementioned U.S. Patents include a constant power control circuit that provides for a generally constant output power while also providing a linear adjustment to account for the unique waveform crest factors associated with different operational modes.

The preferred constant power control circuit and method provided herein allows for output power control by way of a unique and simple linear conversion circuit coupled with protection circuitry that prevents the electrosurgical generator from being over-driven during high and/or low impedance loading. The preferred constant power control circuit also reduces the severity of exit sparking by responding quickly to high impedance indications while nonetheless maintaining substantially increased power levels throughout a predetermined patient tissue impedance range.

SUMMARY OF THE INVENTION

A constant power control circuit for use with an electrosurgical generator. The constant power control circuit and method may be included as an integral part of the overall electrosurgical generator's circuitry, or may be designed as a separate unit that connects to, and controls, an electrosurgical generator. The constant power control circuit and method may be embodied through a variety of analog and/or digital circuit components or arrangements, including software running on computational and memory circuitry.

The constant power control circuit and method maintain the output power of the electrosurgical current at a generally constant level over a finite patient tissue impedance range. The preferred patient tissue impedance range is about 300 to 2500 ohms.

The constant power control circuit and method provide the capability to control the output power of the electrosurgical generator without having to actually monitor the amplitude of both the output current and output voltage. This allows for a simple constant power control circuit and method which operate to control the power output without having to calculate the actual power output of the electrosurgical generator.

While the constant power control circuit may be used to control electrosurgical generators of varying designs, it is preferred that the electrosurgical generator includes a power selection system wherein the user may initialize, set, monitor, and/or control the operation of the electrosurgical generator. It is also preferred that the power selection system produces a control voltage signal that acts to control a high voltage direct current supply which in turn acts to supply a high voltage signal to an output switching radio frequency stage. Then output switching radio frequency stage creates an electrosurgical energy between two output electrodes. The preferred electrosurgical generator need not be limited to these three functional elements, for example the electrosurgical generator could also include additional safety, monitoring, signal modification/conditioning, and/or feedback circuitry or functional elements/processes. The actual electrosurgical generator's design may include the use of digital components and signaling and/or analogue components and signaling, or may be embodied, completely or partially within a software process running on hardware components.

The constant power control circuit includes a current sampling circuit, a linear conversion circuit, and a feedback correction circuit. The current sampling circuit is coupled to one of the output electrodes, and functions so as to produce a sampled current signal that is proportional to the average current flowing through the output electrode.

The linear conversion circuit which is connected to the current sampling circuit internally generates one or more multiplier reference signals and one or more offset reference signals, each of which is used to modify the sampled current signal in accord with the crest factor associated with the electrosurgical energy output by the electrosurgical generator; the modified signal being a linear converted signal.

The feedback correction circuit which is electrically connected to receive the linear converted signal from the linear conversion circuit and the control voltage signal from the power selection system functions to produce a feedback control signal which it then supplies to the power selection system, within the electrosurgical generator, so as to cause the power selection system to control the amount of electrosurgical energy created. The feedback correction circuit functions so as to determine the difference in amplitude between the control voltage signal and the linear converted signal and to then add this difference to the control voltage signal to produce a feedback control signal. The feedback correction circuit may also be connected to the primary transformer winding within the output switching radio frequency stage, or its equivalent, thereby allowing the feedback correction circuit to detect high impedance loading between the output electrodes and to reduce the amplitude of the feedback control signal to protect the circuitry and/or the patient from excessive current and/or voltage levels. A high impedance load is generally considered to be above 2500 ohms. The feedback correction circuit may also include circuitry or processes that substitute another signal for the feedback control signal when the impedance loading between the output electrodes is calculated as being low. A low impedance load is generally considered to be below 300 ohms. Both high and low impedance limits may be adjusted to match the instruments, processes, and/or procedures as necessary.

BRIEF DESCRIPTION OF THE DRAWINGS

FIG. 3 is the preferred embodiment of the feedback correction circuit shown in FIG. 1.

DETAILED DESCRIPTION OF THE INVENTION

Figure 1:
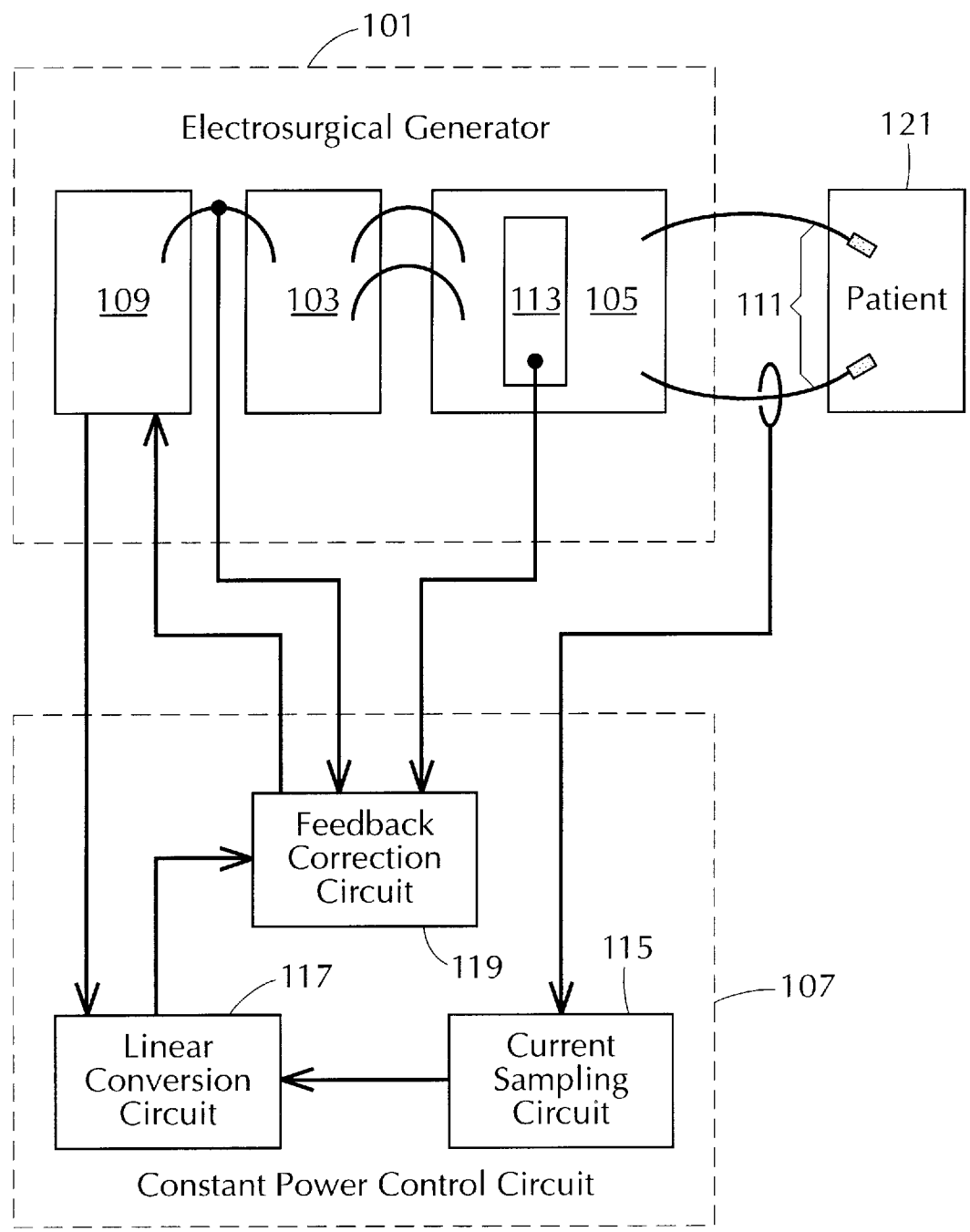
FIG. 1 presents an electrosurgical generator interfaced to a constant power control circuit having a current sampling circuit, linear conversion circuit and feedback correction circuit.

For an electrosurgical generator 101 having a high voltage direct current (DC) supply 103 which is electrically connected to control an output switching radio frequency (RF) stage 105, a unique linear relationship exists between the control voltage supplied to the high voltage DC supply 103 and the root-mean-square (RMS) current generated by the electrosurgical generator 101. This unique linear relationship can be used to design a constant power control circuit 107 that functions as a feedback control loop to control the electrosurgical generator 101. The following mathematical derivations define this unique linear relationship.

It can be shown that:

$$V_{control} = V_{dc}/K_{ps};$$

where, $V_{control}$=a control voltage supplied to the high voltage DC supply, $V_{dc}$=the output voltage signal of the high voltage DC supply, and $K_{ps}$=a feedback ratio of the high voltage DC supply.

It can further be shown that:

$$V_{dc}^2 \times K_a = P_{out};$$

where, $P_{out}$=the output power of the electrosurgical generator 101, and $K_a$=a linear constant (which can be empirically derived).

Therefore, the output power of the electrosurgical generator 101 is directly proportional to the square of the output voltage signal of the high voltage DC supply.

Thus, by substitution:

$$(V_{control} \times K_{ps})^2 \times K_a = P_{out},$$

or $$V_{control}^2 \times K_g = P_{out};$$

where, $$k_g = K_{ps}^2 \times K_a.$$

Therefore, the output power of the electrosurgical generator 101 is proportional to the square of the control voltage supplied to the high voltage DC supply.

Examining the output of the generator we have:

$$P_{out} = V_{rms} \times I_{rms};$$

where, $V_{rms}$=output RMS voltage of the electrosurgical generator 101, and $I_{rms}$=output RMS current of the electrosurgical generator 101.

Accordingly, at a given load impedance =R:

$$V_{rms} = I_{rms} \times R,$$

and by substitution $$P_{out} = I_{rms}^2 \times R.$$

By allowing R to equal a 'matched' load impedance we have $$V_{control}^2 \times K_g = I_{rms}^2 \times R,$$

and therefore $$V_{control}^2 = I_{rms}^2 \times R/K_g.$$

Consequently, for a given impedance $K_r = R/K_g$ the equation can be simplified to:

$$V_{control}^2 = I_{rms}^2 \times K_r.$$

Therefore, the square of the control voltage supplied to the high voltage DC supply 103 is directly proportional to the square of the output RMS current of the electrosurgical generator 101. It can also be shown by similar derivation that the square of the control voltage supplied to the high voltage DC supply 103 is directly proportional to the square of the output RMS voltage of the electrosurgical generator 101.

Thus, the above derivation implies that if either the output RMS current or voltage is sampled properly ($I_{sample}$ & $V_{sample}$ respectively) the control voltage supplied to the high voltage DC supply 103 may be used as a reference value in a feedback control loop to keep either the output RMS current or output RMS voltage constant. When the linear relationship of $I_{rms}$ to $I_{sample}$ is 'mapped' into the linear relationship of $V_{control}$ to $I_{rms}$ then a linear relationship can be derived between $V_{control}$ and $I_{sample}$, When the scaling is done properly for a given power setting, $V_{control}$ will equal $I_{sample}$ at the 'matched' load impedance. Therefore, in a feedback circuit designed with the above mapping a feedback loop which keeps $I_{sample}$ equal to $V_{control}$ will by definition keep $I_{rms}$ constant.

In accord with the above presented mathematical derivation, we have designed a constant power control circuit 107 for the electrosurgical generator 101, shown in FIG. 1, having a power selection system 109 that produces a control voltage signal to control a high voltage direct current supply 103 which supplies a high voltage signal to an output switching radio frequency stage 105 thereby creating an electrosurgical energy between two output electrodes 111. The preferred electrosurgical generator 101 has a plurality of operational modes selectable within the power selection system 109, and a primary transformer winding 113 within the output switching radio frequency stage 105, as shown in FIG. 1.

The constant power control circuit 107, shown in FIG. 1, includes a current sampling circuit 115, a linear conversion circuit 117 and a feedback correction circuit 119.

In the preferred embodiment, the current sampling circuit 115 is inductively coupled to one of the output electrodes 111, as shown in FIG. 1. Alternatively the current sampling circuit 115 could be actively coupled, in circuit, with the output electrode.

The current sampling circuit 115 produces a sampled current signal that is proportional in amplitude to the average current flowing from the electrosurgical generator 101 through the one output electrode, an impedance load 121, and returning to the electrosurgical generator 101 through another output electrode.

The preferred embodiment of the current sampling circuit 115 includes an inductive coil element, similar in design and function to that of a secondary winding of a current transformer. Additional circuit elements function to transform the induced current into a proportional voltage signal and include a voltage drop resistor, a calibrating variable resistor, and elements that rectify and average the sampled current signal.

The current sampling circuit 115 supplies the sampled current signal to the linear conversion circuit 117. However, before the sampled current signal can be used as a feedback term, the mode crest factor for the selected electrosurgical generator 101 operational mode, needs to be compensated for. The linear conversion circuit 117, in FIGS. 1 and 2, compensates for the linear relationship between the sampled current signal and a 'true' sampled RMS value, which is of the form $I_{rms} = m \times I_{sample} + b$, where $I_{rms}$ is a signal which is directly proportional to the RMS current, and m and b are given constants derived for a given crest factor. While electrosurgical generators 101 have a wide variety of different output wave shapes with varying crest factors, it is preferred that the crest factor for a given mode be significantly constant over a finite patient tissue impedance range, such as between 300 and 2500 ohms.

Accordingly, the linear conversion circuit 117 first multiples the sampled current signal by the gain, m, and then adds the offset to it, b. When the values of m and b are chosen properly the resulting linear converted signal is directly proportional to the output RMS current of the electrosurgical generator 101. The preferred method for determining the proper values of m and b for a given operational mode and electrosurgical generator 101 includes collecting empirical data on the control voltage supplied to the high voltage DC supply 103 and the resulting output RMS current of the electrosurgical generator 101 and solving the linear equation, for m and b, by substitution.

Figure 2:
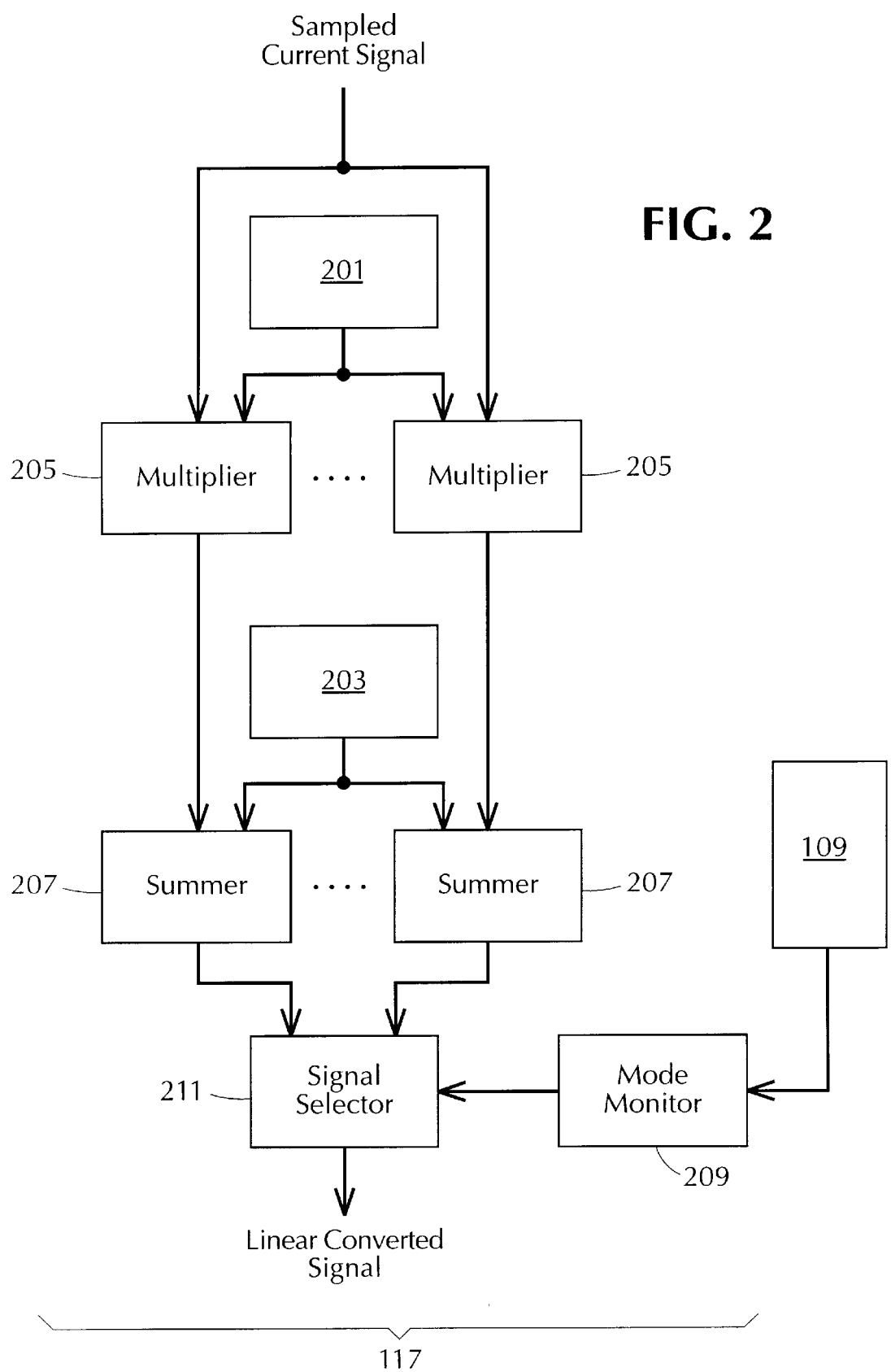
FIG. 2 is the preferred embodiment of the linear conversion circuit shown in FIG. 1.

The linear conversion circuit 117, shown in FIGS. 1 and 2, is electrically connected to the current sampling circuit 115. In the preferred embodiment, the linear conversion circuit 117 is also electrically connected to the power selection system 109 such that the operational mode of the electrosurgical generator 101 can be determined based on this connection. The linear conversion circuit 117 generates a linear converted signal and supplies this signal to the feedback correction circuit 119.

The preferred embodiment includes a linear multiplier generating means 201 within the linear conversion circuit 117, see FIG. 2. The linear multiplier generating means 201 generates a plurality of unique multiplier reference signals (i.e., a factor 'm'). There is preferably one, unique, multiplier reference signal for each operational mode. The preferred embodiment, of the linear multiplier generating means 201 includes several resistive components connected to voltage sources, across which a predetermined voltage is maintained.

The preferred embodiment includes a linear offset generating means 203 within the linear conversion circuit 117, see FIG. 2. The linear offset generating means 203 generates a plurality of unique offset reference signals (i.e., a factor 'b'). There is preferably one, unique, offset reference signal for each operational mode. The preferred embodiment of the linear offset generating means 203 includes several resistive components connected to voltage sources, across which a predetermined voltage is maintained.

The preferred embodiment also includes a plurality of multipliers 205, within the linear conversion circuit 117, see FIG. 2. There is preferably one, corresponding, multiplier 205 for each operational mode. Each multiplier 205 is electrically connected to receive the sampled current signal and one unique multiplier reference signal from the linear multiplier generating means 201. Each multiplier 205 multiplies the sampled current signal and the unique multiplier reference signal associated with one operational mode to produce a unique multiplied signal for that operational mode. The preferred embodiment of the multiplier 205 includes a plurality of operational amplifiers.

The preferred embodiment includes a plurality of summers 207, within the linear conversion circuit 117, see FIG. 2. There is preferably one, corresponding, summer 207 for each operational mode. Each summer 207 is electrically connected to receive a unique multiplied signal and one unique offset reference signal from the linear offset generating means 203. Each summer 207 sums the offset reference signal associated with one operational mode and the unique multiplied signal associated with that operational mode to produce a unique linear converted signal for that operational mode. The preferred embodiment of the summer 207 includes configuring the plurality of operational amplifiers used as multipliers 205 to also function as summers 207.

The preferred embodiment includes a mode monitor 209, within the linear conversion circuit 117, see FIG. 2. The mode monitor 209 is electrically connected to the power selection system 109, for identifying the operational mode of the electrosurgical generator 101 and producing an identified operational mode signal therefrom.

Closely associated with the mode monitor 209, is a signal selector 211 that is also within the linear conversion circuit 11 7, see FIG. 2. The signal selector 211 is electrically connected to receive the identified operational mode signal and the unique linear converted signal from each of the summers 207. The signal selector 211 selects the unique linear converted signal associated with the identified operational mode, and causes that linear converted signal to be supplied to the feedback correction circuit 119. In the preferred embodiment the mode monitor 209 and signal selector 211 are embodied within a circuit including a digital processing component that activates and/or deactivates a plurality of electronic switching elements.

The feedback correction circuit 119, shown in FIGS. 1 and 3, is electrically connected to receive the linear converted signal from the linear conversion circuit 117, the control voltage signal from the power selection system 109, and the voltage signal across the primary transformer winding 113. The feedback correction circuit 119 produces a feedback control signal and supplies the feedback control signal to the power selection system 109 so as to control the amount of electrosurgical energy created by the electrosurgical generator 101.

The feedback correction circuit 119 includes a subtractor 301, see FIG. 3. The subtractor 301 is electrically connected to receive the linear converted signal from the linear conversion circuit 117 and the control voltage signal which is generated by the power selection system 109 and supplied to the high voltage DC supply, see FIGS. 1 and 3. The subtractor 301 determines the difference in amplitude between the control voltage signal and the linear converted signal, and produces a delta signal proportional to the difference. The preferred embodiment of the subtractor 301 includes an operational amplifier component.

Also included in the feedback correction circuit 119 is an adder 303, see FIG. 3. The adder 303 is electrically connected to receive the delta signal and the control voltage signal. The adder 303 adds the delta signal to the control voltage signal to produce the feedback control signal. The preferred embodiment includes an operational amplifier component.

Since holding the output RMS current constant for all impedances would be a physical impossibility based on the design limitations of the high voltage DC supply 103 and the output switching RF stage 105, it is preferred that the feedback control signal to the high voltage DC supply 103 be limited as a function of the impedance load 121 between the output electrodes 111.

In the preferred embodiment, the feedback correction circuit 119 includes a maximum control voltage reference generator 305 for generating a maximum control voltage reference signal, see FIG. 3. The preferred embodiment uses an operational amplifier component connected to the control voltage signal to establish a maximum control voltage reference signal based thereon.

The maximum control voltage reference signal is supplied to a switcher 307 within the preferred feedback correction circuit 119, see FIG. 3. The switcher 307 is also electrically connected to receive the feedback control signal from the adder 303. The switcher 307 substitutes the maximum control voltage reference signal for the feedback control signal when the feedback control signal is greater in amplitude than the maximum control voltage reference signal, thereby limiting the electrosurgical generator's 101 output current through the output electrodes 111 when the impedance load 121 is at a low impedance level. The preferred embodiment of the switcher 307 includes an AND circuit created with diodes that passes the lower of the two signals as the feedback control signal.

When the impedance load 121 between the output electrodes 111 is high, the preferred constant power control circuit 107 should limit the output voltage of the electrosurgical generator 101 so as protect the electrosurgical generator 101, and reduce leakage currents and exit sparking.

In the preferred embodiment, the feedback correction circuit 119 shown in FIG. 3, includes a high impedance reference generator 309 for generating a high impedance reference signal. The high impedance reference generator 309 is electrically connected to receive the control voltage signal. The preferred high impedance reference generator 309 establishes the high impedance reference signal by linearly converting the control voltage signal with an operational amplifier.

In the preferred embodiment a connector 311 is used for electrically connecting a comparator 313, within the feedback correction circuit 119, to the primary transformer winding 113, see FIGS. 1 and 3. The connector 311 provides the comparator 313 with the voltage across the primary transformer winding 113. The comparator 313 is also electrically connected to receive the high impedance reference signal. The comparator 313 compares the amplitude of the high impedance reference signal to the voltage across the primary transformer winding 113 and produces a high impedance detection signal that indicates the results of this comparison. In the preferred embodiment the comparator 313 includes an operational amplifier component.

The high impedance detection signal is received by a reducer 315, shown in FIG. 3 of the preferred embodiment, which is electrically connected to the comparator 313 and to the switcher 307. The reducer 315 reduces, to an internally generated preset reduced voltage level signal, the amplitude of the feedback control signal from the switcher 307 when the voltage across the primary transformer winding 113 is greater than the high impedance reference signal as indicated by the high impedance detection signal. In the preferred embodiment, the reducer 315 includes a logic driven switched circuit and an adjustable resistor providing a reduced voltage level signal. The reducer 315 supplies the resulting feedback control signal to the power selection system 109.

Associated with the constant power control circuit 107 is a method for maintaining a generally constant output power from an electrosurgical generator 101 having a power selection system 109 that produces a control voltage signal to control a high voltage direct current supply 103 which supplies a high voltage signal to an output switching radio frequency stage 105 thereby creating an electrosurgical energy between two output electrodes 111.

The method includes the steps of inductively coupling to one output electrode, sensing the current flowing through the output electrode 111 and producing a sampled current signal proportional to the average current flowing through the output electrode. The method then continues with the steps of generating a multiplier reference signal, generating an offset reference signal, multiplying the sampled current signal and the multiplier reference signal, and then summing the offset reference signal to the product to producing a linear converted signal.

The method continues with the steps of connecting to the control voltage signal from the power selection system 109, determining the difference in amplitude between the control voltage signal and the linear converted signal, adding the difference determined by the subtraction means to the control voltage signal to produce a feedback control signal, and then supplying the feedback control signal to the power selection system 109 to control the amount of electrosurgical energy created.

To protect the electrosurgical generator 101 and the patient when the impedance load 121 is high, the method can include the steps of generating a high impedance reference signal, connecting to the primary transformer winding 113, comparing the amplitude of the high impedance reference signal to the voltage across the primary transformer winding 113, and reducing the amplitude of the feedback control signal when the voltage across the primary transformer winding 113 is greater than the high impedance reference signal.

To protect the electrosurgical generator 101 and patient when the impedance load 121 is low, the method can include the steps of generating a maximum control voltage reference signal and substituting the maximum control voltage reference signal for the feedback control signal when the feedback control signal is greater in amplitude than the maximum control voltage reference signal.

For electrosurgical generators 101 having a plurality of operational modes, the method can be modified to include the steps of generating a plurality of unique linear multiplier reference signals, one for each operational mode, and generating a plurality of unique linear offset reference signals, one for each operational mode. The method would then include the steps of multiplying the sampled current signal, separately and concurrently, with each of the unique multiplier reference signals to produce a plurality of unique multiplied signals, one for each operational mode, and then summing each of the unique multiplied signals with the offset reference signal associated with the same operational mode to produce a plurality of unique linear converted signals, one for each operational mode. The method would continue with the steps of connecting to the power selection system 109 to identify the operational mode selected, selecting the unique linear converted signal that matches the identified operational mode, and then causing that linear converted signal to be supplied to the feedback correction circuit 119.

What is claimed is:

1. A constant power control circuit for use in an electrosurgical generator having a power selection system that produces a control voltage signal to control a high voltage direct current supply which supplies a high voltage signal to an output switching radio frequency stage thereby creating an electrosurgical energy between two output electrodes, the constant power control circuit comprising:

a current sampling circuit inductively coupled to one output electrode, the current sampling circuit producing a sampled current signal proportional to an average current flowing through the output electrode;

a linear conversion circuit electrically connected to the current sampling circuit for generating a linear converted signal, wherein the linear conversion circuit includes;

a linear multiplier generating means for generating a multiplier reference signal;

a linear offset generating means for generating an offset reference signal;

a multiplier, electrically connected to the linear multiplier generating means, for multiplying the sampled current signal and the multiplier reference signal to produce a multiplied signal; and a summer, electrically connected to the linear offset generating means, for summing the offset reference signal and the multiplied signal to produce the linear converted signal; and a feedback correction circuit electrically connected to receive the linear converted signal from the linear conversion circuit and the control voltage signal from the power selection system for producing a feedback control signal which is supplied to the power selection system to control the amount of electrosurgical energy created, wherein the feedback correction circuit includes:

a subtractor, electrically connected to receive the linear converted signal and the control voltage signal, for determining a difference in amplitude between the control voltage signal and the linear converted signal and producing a delta signal proportional to the difference; and an adder, electrically connected to receive the delta signal and the control voltage signal, for adding the delta signal to the control voltage signal and producing the feedback control signal.

2. The constant power control circuit for an electrosurgical generator having a power selection system that produces a control voltage signal to control a high voltage direct current supply which supplies a high voltage signal to an output switching radio frequency stage thereby creating an electrosurgical energy between two output electrodes of claim 1, wherein the output switching radio frequency stage has a primary transformer winding, and wherein the feedback correction circuit further includes:

a high impedance reference generator, electrically connected to receive the control voltage signal, for generating a high impedance reference signal;

a connector for electrically connecting the feedback correction circuit to the primary transformer winding;

a comparator, electrically connected to the connector and to receive the high impedance signal, for comparing the amplitude of the high impedance reference signal to the voltage across the primary transformer winding and producing a high impedance detection signal; and a reducer, electrically connected to receive the high impedance detection signal and the feedback control signal, for reducing the amplitude of the feedback control signal when the high impedance detection signal indicates that the voltage across the primary transformer winding is greater than the high impedance reference signal.

3. The constant power control circuit for an electrosurgical generator having a power selection system that produces a control voltage signal to control a high voltage direct current supply which supplies a high voltage signal to an output switching radio frequency stage thereby creating an electrosurgical energy between two output electrodes of claim 1, wherein the feedback correction circuit further includes:

a maximum control voltage reference generator, electrically connected to receive the control voltage signal, for generating a maximum control voltage reference signal; and a switcher, electrically connected to receive the maximum control voltage reference signal and the feedback control signal, for substituting the maximum control voltage reference signal for the feedback control signal when the feedback control signal is greater in amplitude than the maximum control voltage reference signal.

4. The constant power control circuit for an electrosurgical generator having a power selection system that produces a control voltage signal to control a high voltage direct current supply which supplies a high voltage signal to an output switching radio frequency stage thereby creating an electrosurgical energy between two output electrodes of claim 1, wherein the power selection system has a plurality of operational modes and wherein the linear multiplier generating means generates a unique multiplier reference signal for each operational mode, and the linear offset generating means generates a unique offset reference signal for each operational mode, and wherein the linear conversion circuit further includes:

a plurality of multipliers, wherein there is one multiplier for each operational mode and each multiplier multiplies the sampled current signal and the unique multiplier reference signal associated with one operational mode to produce a unique multiplied signal for that operational mode;

a plurality of summers, wherein there is one summer for each operational mode and each summer sums the offset reference signal associated with one operational mode and the unique multiplied signal associated with that operational mode to produce a unique linear converted signal for that operational mode;

a mode monitor, adapted to be electrically connected to the power selection system, for identifying the operational mode and producing an identified operational mode signal;

a signal selector, electrically connected to receive the identified operational mode signal and the unique linear converted signal from each of the summers, for selecting the unique linear converted signal associated with the identified operational mode, and causing that linear converted signal to be supplied to the feedback correction circuit.

5. A constant power control circuit for an electrosurgical generator having a power selection system that produces a control voltage signal to control a high voltage direct current supply which supplies a high voltage signal to an output switching radio frequency stage thereby creating an electrosurgical energy between two output electrodes, wherein the power selection system has a plurality of operational modes and the output switching radio frequency stage has a primary transformer winding, and wherein the constant power control circuit comprises:

a current sampling circuit adapted to be inductively coupled to one output electrode, the current sampling circuit producing a sampled current signal proportional to an average current flowing through the output electrode;

a linear conversion circuit electrically connected to the current sampling circuit for generating a linear converted signal, wherein the linear conversion circuit includes;

a linear multiplier generating means for generating a plurality of unique multiplier reference signals, wherein there is one multiplier reference signal for each operational mode;

a linear offset generating means for generating a plurality of unique offset reference signals, wherein there is one offset reference signal for each operational mode;

a plurality of multipliers, electrically connected to the linear multiplier generating means and to receive the sampled current signal, wherein there is one multiplier for each operational mode and each multiplier multiplies the sampled current signal and the unique multiplier reference signal associated with one operational mode to produce a unique multiplied signal for that operational mode;

a plurality of summers, electrically connected to the linear offset generating means and to each multiplier, wherein there is one summer for each operational mode and each summer sums the offset reference signal associated with one operational mode and the unique multiplied signal associated with that operational mode to produce a unique linear converted signal for that operational mode;

a mode monitor, adapted to be electrically connected to the power selection system, for identifying the operational mode and producing an identified operational mode signal;

a signal selector, electrically connected to receive the identified operational mode signal and the unique linear converted signal from each of the summers, for selecting the unique linear converted signal associated with the identified operational mode, and causing that linear converted signal to be supplied to the feedback correction circuit; and a feedback correction circuit electrically connected to receive the linear converted signal from the linear conversion circuit and adapted to receive the control voltage signal from the power selection system for producing a feedback control signal which is adapted to be supplied to the power selection system to control the amount of electrosurgical energy created, wherein the feedback correction circuit includes:

a subtractor, electrically connected to receive the linear converted signal and the control voltage signal, for determining a difference in amplitude between the control voltage signal and the linear converted signal and producing a delta signal proportional to the difference;

an adder, electrically connected to receive the delta signal and the control voltage signal, for adding the delta signal to the control voltage signal and producing the feedback control signal;

a maximum control voltage reference generator, electrically connected to receive the control voltage signal, for generating a maximum control voltage reference signal;

a switcher, electrically connected to receive the maximum control voltage reference signal and the feedback control signal, for substituting the maximum control voltage reference signal for the feedback control signal when the feedback control signal is greater in amplitude than the maximum control voltage reference signal a high impedance reference generator, electrically connected to receive the control voltage signal, for generating a high impedance reference signal;

a connector adapted for electrically connecting the feedback correction circuit to the primary transformer winding;

a comparator, electrically connected to the connector and to receive the high impedance signal, for comparing the amplitude of the high impedance reference signal to the voltage across the primary transformer winding and producing a high impedance detection signal; and a reducer, electrically connected to receive the high impedance detection signal and the feedback control signal, for reducing the amplitude of the feedback control signal when the high impedance detection signal indicates that the voltage across the primary transformer winding is greater than the high impedance reference signal.

6. A method for maintaining a generally constant output power from an electrosurgical generator having a power selection system that produces a control voltage signal to control a high voltage direct current supply which supplies a high voltage signal to an output switching radio frequency stage thereby creating an electrosurgical energy between two output electrodes, the method including the steps of:

inductively coupling to one output electrode;

sensing the current flowing through the output electrode;

producing a sampled current signal proportional to the average current flowing through the output electrode;

generating a multiplier reference signal;

generating an offset reference signal;

multiplying the sampled current signal and the multiplier reference signal; then summing the offset reference signal to the product to produce a linear converted signal;

connecting to the control voltage signal from the power selection system;

determining the difference in amplitude between the control voltage signal and the linear converted signal;

adding the difference determined by the subtraction means to the control voltage signal to produce a feedback control signal, and supplying the feedback control signal to the power selection system to control the amount of electrosurgical energy created.

7. The method for maintaining a generally constant output power from an electrosurgical generator having a power selection system that produces a control voltage signal to control a high voltage direct current supply which supplies a high voltage signal to an output switching radio frequency stage thereby creating an electrosurgical energy between two output electrodes of claim 6, wherein the output switching radio frequency stage has a primary transformer winding, and wherein the method further includes the steps of:

generating a high impedance reference signal;

connecting to the primary transformer winding;

comparing the amplitude of the high impedance reference signal to the voltage across the primary transformer winding; and reducing the amplitude of the feedback control signal when the voltage across the primary transformer winding is greater than the high impedance reference signal.

8. The method for maintaining a generally constant output power from an electrosurgical generator having a power selection system that produces a control voltage signal to control a high voltage direct current supply which supplies a high voltage signal to an output switching radio frequency stage thereby creating an electrosurgical energy between two output electrodes of claim 6, the method further including the steps of:

generating a maximum control voltage reference signal; and substituting the maximum control voltage reference signal for the feedback control signal when the feedback control signal is greater in amplitude than the maximum control voltage reference signal.

9. The method for maintaining a generally constant output power from an electrosurgical generator having a power selection system that produces a control voltage signal to control a high voltage direct current supply which supplies a high voltage signal to an output switching radio frequency stage thereby creating an electrosurgical energy between two output electrodes of claim 6, wherein the power selection system has a plurality of operational modes and wherein the method further includes the steps of:

generating a plurality of unique linear multiplier reference signals, one for each operational mode;

generating a plurality of unique linear offset reference signals, one for each operational mode;

multiplying the sampled current signal, separately and concurrently, with each of the unique multiplier reference signals to produce a plurality of unique multiplied signals, one for each operational mode;

summing each of the unique multiplied signals with the offset reference signal associated with the same operational mode to produce a plurality of unique linear converted signals, one for each operational mode;

connecting to the power selection system to identify the operational mode selected;

selecting the unique linear converted signal that matches the identified operational mode; and then causing that linear converted signal to be supplied to the feedback correction circuit.

* * * * *